US012629439B2

(12) United States Patent
Salkic

(10) Patent No.: US 12,629,439 B2
(45) Date of Patent: May 19, 2026

(54) DISINFECTION SYSTEM

(71) Applicant: MERCEDES-BENZ GROUP AG, Stuttgart (DE)

(72) Inventor: Asmir Salkic, Ulm (DE)

( * ) Notice: Subject to any disclaimer, the term of this patent is extended or adjusted under 35 U.S.C. 154(b) by 581 days.

(21) Appl. No.: 18/020,663

(22) PCT Filed: Jul. 23, 2021

(86) PCT No.: PCT/EP2021/070702
§ 371 (c)(1),
(2) Date: Feb. 10, 2023

(87) PCT Pub. No.: WO2022/033840
PCT Pub. Date: Feb. 17, 2022

(65) Prior Publication Data
US 2024/0033383 A1     Feb. 1, 2024

(30) Foreign Application Priority Data

Aug. 11, 2020     (DE) ..................... 10 2020 004 883.8

(51) Int. Cl.
A61L 2/10      (2026.01)
B60Q 3/68      (2017.01)
B60Q 3/80      (2017.01)
*A61L 103/75*      (2026.01)

(52) U.S. Cl.
CPC .................. *A61L 2/10* (2013.01); *B60Q 3/68* (2017.02); *B60Q 3/80* (2017.02); *A61L 2103/75* (2026.01); *A61L 2202/11* (2013.01); *A61L 2202/14* (2013.01)

(58) Field of Classification Search
CPC .... A61L 2/10; A61L 2202/11; A61L 2202/14; A61L 2205/25; B60Q 3/68; B60Q 3/80; B60Q 3/208
See application file for complete search history.

(56) References Cited

U.S. PATENT DOCUMENTS

| | | | |
|---|---|---|---|
| 9,492,575 B2 | 11/2016 | Holub et al. | |
| 9,993,571 B2 | 6/2018 | Lin et al. | |
| 10,639,390 B2 * | 5/2020 | Lloyd ...................... | A61L 2/10 |
| 10,933,821 B2 | 3/2021 | Line et al. | |

(Continued)

FOREIGN PATENT DOCUMENTS

| | | |
|---|---|---|
| CN | 106237351 A | 12/2016 |
| DE | 102012006972 A1 | 10/2013 |

(Continued)

OTHER PUBLICATIONS

Office Action dated Aug. 9, 2024 in related/corresponding KR Application No. 10-2023-7004078.

(Continued)

*Primary Examiner* — Regina M Yoo
(74) *Attorney, Agent, or Firm* — PATENT PORTFOLIO BUILDERS PLLC

(57) ABSTRACT

A disinfection system for a vehicle includes a a first light source for an interior of the vehicle for generating radiation in the UV-B and/or UV-C range and a second light source for generating radiation in the UV-C range. Whether the first or second light source is used to disinfect the interior of the vehicle depends on whether or not there is an occupant in the vehicle.

13 Claims, 1 Drawing Sheet

(56) References Cited

U.S. PATENT DOCUMENTS

| | | | |
|---|---|---|---|
| 2015/0273092 A1 | 10/2015 | Holub et al. | |
| 2017/0304472 A1* | 10/2017 | Neister | A23B 7/015 |
| 2018/0015192 A1 | 1/2018 | Salter et al. | |
| 2018/0055959 A1 | 3/2018 | Lin et al. | |
| 2018/0209613 A1* | 7/2018 | Callahan | A61L 2/10 |
| 2018/0369434 A1 | 12/2018 | Callahan | |
| 2019/0060496 A1* | 2/2019 | Tillotson | A61L 2/24 |
| 2019/0076558 A1 | 3/2019 | Zhang-Miske et al. | |
| 2020/0061223 A1 | 2/2020 | Hallack | |
| 2021/0015959 A1 | 1/2021 | Goseki et al. | |
| 2021/0316022 A1* | 10/2021 | Ciesiun | A61L 2/10 |
| 2021/0346561 A1* | 11/2021 | Callahan | A61L 2/28 |
| 2021/0361810 A1* | 11/2021 | Glanz | A61L 2/24 |
| 2021/0393820 A1* | 12/2021 | Childress | B64F 5/30 |
| 2022/0023468 A1* | 1/2022 | Sears | B64D 11/00 |

FOREIGN PATENT DOCUMENTS

| | | | |
|---|---|---|---|
| DE | 102017115060 A1 | 1/2018 | |
| DE | 102018002328 A1 | 9/2019 | |
| DE | 102020108301 A1 | 10/2020 | |
| EP | 2668964 A1 | 12/2013 | |
| JP | 2018069029 A | 5/2018 | |
| JP | 2018114197 A | 7/2018 | |
| WO | 2019139743 A1 | 7/2019 | |
| WO | 2019186880 A1 | 10/2019 | |
| WO | WO-2019246394 A1 * | 12/2019 | A61L 2/28 |

OTHER PUBLICATIONS

Notice of Reasons for Refusal dated Dec. 26, 2023 in related/corresponding JP Application No. 2023-507870.

Office Action dated May 12, 2025 in related/corresponding CN Application No. 202180055986.0.

International Search Report and Written Opinion mailed Nov. 18, 2021 in related/corresponding International Application No. PCT/EP2021/070702.

Office Action created Jun. 3, 2021 in related/corresponding DE Application No. 10 2020 004 883.8.

Office Action dated Jun. 26, 2025 in related/corresponding KR Application No. 10-2023-7004078.

Intention to Grant dated Jan. 16, 2024 in related/corresponding EP Application No. 21 754 937.7.

* cited by examiner

DISINFECTION SYSTEM

BACKGROUND AND SUMMARY OF THE INVENTION

Exemplary embodiments of the invention relate to a disinfection system for a vehicle, as well as to a method for controlling the disinfection system and to a vehicle having the disinfection system.

Conventional vehicles do not have any disinfection systems that enable an automatic and fast disinfection. For this reason, the vehicles are disinfected manually and with significant effort with chemicals as required. The need for an automatic and quick disinfection to prevent the transfer of viruses and bacteria from a passenger to another passenger is particularly present for rental vehicles.

It is known that electromagnetic radiation in the UV range has a disinfecting effect. If viruses, bacteria, or protozoa are exposed to UV radiation in the wavelength range of 200-300 nm, they lose their ability to reproduce and infect. UV radiation is increasingly used for environmentally-friendly, chemical-free, and highly effective disinfection. One disadvantage is that UV radiation in the wavelength range of 200-300 nm is also potentially harmful for human skin and the human eye.

DE 10 2017 115 060 A1 discloses using a light source to generate electromagnetic radiation in the UV-B range in a vehicle. Vitamin D production can thus be intensified for passengers, and germs—and thus viruses and bacteria—can be killed. A disadvantage of the radiation in the UV-B range is that it has a weak disinfecting effect.

Exemplary embodiments of the invention thus provide an improved, or at least an alternative embodiment for a generic disinfection system in which the disadvantages described are overcome. Exemplary embodiments of the invention also provide a method for controlling the disinfection system, and a motor vehicle having the disinfection system.

The disinfection system is provided for a vehicle. This disinfection system has a first light source for an interior of the vehicle that is designed to generate radiation in the UV range. According to the invention, the first light source is designed to generate radiation in the UV-B and/or UV-C range. The disinfection system also additionally has a second light source that is designed to generate radiation in the UV-C range.

In the present invention, the term "radiation" is always understood to mean electromagnetic radiation or light. The abbreviation UV stands for the term "ultraviolet". The specified UV-B range and the specified UV-C range relate to wavelengths of the electromagnetic radiation in the UV range. According to the usual definition, the wavelengths of the electromagnetic radiation in the UV-B range are between 315-280 nm and the wavelengths of the radiation in the UV-C range are between 280-100 nm. The unit "nm" used here and in the following stands for nanometers.

The first light source is formed to generate radiation in the range of 100-300 nm here. The first light source is preferably formed to generate radiation in the range of 200-300 nm. The second light source is formed to generate radiation in the range of 210-230 nm. The second light source is preferably formed to generate radiation in the range of 222 nm.

The first light source irradiates within a broad UV range and can be employed to disinfect the empty vehicle or the vehicle without passengers. The second light source irradiates within a narrow UV range, and is thus safe for human skin and the human eye. The second light source can thus be employed to disinfect the occupied vehicle or the vehicle with passengers. The interior of the vehicle can be disinfected without contact, without chemicals, and effectively using the disinfection system according to the invention. The disinfection can also advantageously be achieved highly effectively in an occupied vehicle or in a vehicle with passengers.

It can advantageously be provided that the second light source is formed to generate radiation having a radiation concentration of at least 12 mJ/cm². A regeneration of viruses and bacteria can thus be effectively prevented. The exact radiation concentration of the radiation can be determined based on field tests or bioassay validation here. The unit "mJ" used here and in the following stands for millijoules. The unit "cm" used stands for centimeters here and in the following.

The disinfection system can advantageously have a controller that controls the first light source and the second light source. The controller can particularly be formed to carry out the method for controlling the disinfection system. The controller of the disinfection system can be a part of an artificial intelligence (AI) system, for example. The controller can particularly switch the two light sources on and off. Switching the respective light source on and off can here occur depending on whether the disinfection should take place of the empty vehicle or the vehicle without passengers or of the occupied vehicle or the vehicle with passengers. The disinfection system can preferably have at least one identification unit for identifying passengers in the vehicle. The identification unit is preferably a camera or a radar.

The first light source and/or the second light source can advantageously be formed as one part or as several parts. In other words, the first light source and/or the second light source can respectively consist of one lighting unit or several lighting units. The first light source and/or the second light source can advantageously have several parts and be arranged distributed in the interior of the vehicle. The arrangement of the individual lighting units in the interior of the vehicle can occur in such a manner here that the entire interior of the vehicle can be irradiated by the first light source and by the second light source.

In summary, a contact-free and safe disinfection of the interior of the vehicle can occur via the disinfection system according to the invention. The disinfection can occur in an environmentally-friendly, chemical-free, sustainable, and highly effective manner here. The storage, transport, and handling of poisonous chemicals are not required in the disinfection system according to the invention, and no chemical by-products, particularly carcinogenic by-products are created. There is additionally no danger of corrosion for the vehicle.

Exemplary embodiments of the invention also relate to a method for controlling a disinfection system described above. In the method, a controller of the disinfection system first determines whether there are passengers in the vehicle by means of at least one identification unit. The identification unit is preferably a camera or a radar. The controller switches on the first light source or the second light source depending on whether there are passengers in the vehicle.

It can advantageously be provided that, if there are no passengers in the vehicle, the controller switches on the first light source for at least 6 seconds. As described above, the first light source can be formed to generate radiation in the range of 100-300 nm here. The first light source is preferably formed to generate radiation in the range of 200-300 nm. A safe and almost complete elimination of viruses and bacteria can be brought about with the first light source. As the radiation in the range of 200-300 nm can be dangerous for human skin and for the human eye, the first light source is switched on when there are no passengers in the vehicle. This accordingly prevents the passengers from being injured.

It can advantageously be provided that, if there are passengers in the vehicle, the controller switches on the second light source for at least 2.5 seconds. As described above, the second light source can be formed to generate radiation in the range of 210-230 nm. The second light source is preferably provided to generate radiation in the range of 222 nm. The radiation in the range of 222 nm is less harmful for human skin and for the human eye than the radiation in the broad range of 200-300 nm. Most viruses and bacteria are nevertheless eliminated.

The disinfection can occur in the empty vehicle or in the vehicle without passengers and in the occupied vehicle or in the vehicle with passengers with the method according to the invention. The disinfection can thus occur at any point in time, and the passengers can be better protected against viruses and bacteria. The disinfection system can be operated automatically here. The disinfection system can additionally be operated in an energy-efficient manner, or the maximum disinfection effect can be achieved with the minimum energy usage.

Exemplary embodiments of the invention also relate to a vehicle having a disinfection system described above. The first light source and the second light source are fixed in an interior of the vehicle on a roof of the vehicle and/or on a bearing column of the vehicle and/or on a console of the vehicle here. The first light source and the second light source can advantageously be arranged next to each other in such a manner that the radiation propagation of the first light source and the radiation propagation of the second light source are identical within the interior of the vehicle. Every region of the interior of the vehicle is thus irradiated with the first light source and the second light source. The disinfection of the interior of the vehicle can thus occur with the first light source and with the second light source in the same manner completely and efficiently.

Further important features and advantages of the invention result from the drawings and from the associated description of figures with reference to the drawings.

Naturally, the features specified previously and remaining to be explained in the following can be used not only in the respectively given combinations, but also in other combinations or in isolation without leaving the scope of the present invention.

BRIEF DESCRIPTION OF THE DRAWING FIGURES

Preferred exemplary embodiments of the invention are depicted in the drawings and are explained in more detail in the following description, wherein identical reference numerals relate to identical or similar or functionally similar components.

In the following:

DETAILED DESCRIPTION

Figure 1:
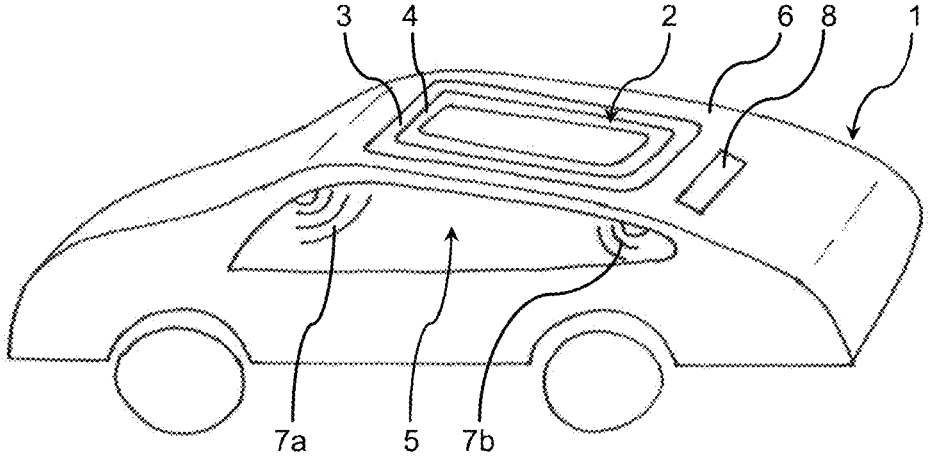
FIG. 1 shows a schematic view of a vehicle having a disinfection system according to the invention.

FIG. 1 shows a schematic view of a vehicle 1 having a disinfection system 2 according to the invention. The disinfection system 2 has a first light source 3 and a second light source 4 here, which are fixed on a roof 6 in an interior 5 of the vehicle 1. The first light source 3 and the second light source 4 are arranged next to each other, such that the radiation propagation of the first light source 3 and the radiation propagation of the second light source 4 are identical within the interior 5 of the vehicle 1.

The first light source 3 is designed to generate radiation in the UV-B and/or UV-C range. The first light source 3 can advantageously be formed to generate radiation in the range of 100-300 nm here. The first light source 3 is preferably formed to generate radiation in the range of 200-300 nm. The first light source 3 irradiates within a broad UV range and can be employed to disinfect the empty vehicle 1 or the vehicle 1 without passengers.

The second light source 4 is designed to generate radiation in the UV-C range. The second light source 4 can advantageously be formed to generate radiation in the range of 210-230 nm. The second light source 4 is preferably formed to generate radiation in the range of 222 nm. The second light source 4 irradiates within a narrow UV range and can be employed to disinfect the occupied vehicle 1 or the vehicle 1 with passengers. The second light source 4 is appropriately formed to generate radiation having a radiation concentration of at least 12 mJ/cm$^2$ in order to enable a safe disinfection of the interior 5.

The disinfection system 2 additionally has two identification units 7a and 7b, wherein the identification units 7a and 7b are formed as cameras/radars here. The disinfection system 2 can determine via the identification units 7a and 7b whether there are passengers in the interior 5 or not. A controller 8 of the disinfection system 2 can control the light sources 3 and 4 on this basis.

Figure 2:
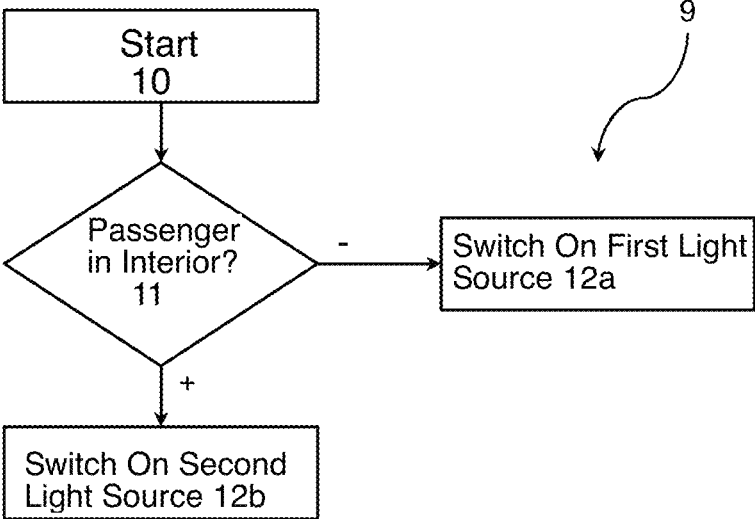
FIG. 2 shows a control schematic diagram of a method according to the invention for controlling the disinfection system.

Controlling the disinfection system 2 occurs in a method 9 according to the invention. FIG. 2 shows a control schematic diagram of the method 9 here. After a starting step 10, the controller 8 determines whether passengers are or are remaining in the interior 5 of the vehicle 1 by means of the identification units 7a and 7b in an identification step 11.

If there are no passengers in the interior 5 of the vehicle 1—labelled with "−" in FIG. 2—then a disinfection step 12a is carried out. The first light source 3 is switched on for disinfecting the interior 5 for 6 seconds here, and a thorough disinfection of the interior 5 is undertaken. If there are passengers in the interior 5—labelled with "+" in FIG. 2—then a disinfection step 12b is carried out. The second light source 4 is switched on for disinfecting the interior 5 for 2.5 seconds here, and a disinfection of the interior 5 that is safe for human skin and the human eye is undertaken.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A disinfection system for a vehicle, the disinfection system comprising:
a first light source arranged in an interior of the vehicle and configured to generate radiation in a range of 100-300 nm;
a second light source arranged in the interior of the vehicle and configured to generate radiation in a range of 210-230 nm;
at least one identification unit configured to identify whether there are passengers in the vehicle; and
a controller configured to control the first and second light sources based on whether there are passengers in the vehicle so that when there are no passengers in the vehicle the controller activates the first light source for a first period of time and when there are passengers in the vehicle the controller activates the second light source for a second period of time.

2. The disinfection system of claim 1, wherein the first light source is configured to generate radiation in a range of 200-300 nm and the second light source is configured to generate radiation in the range of 222 nm.

3. The disinfection system of claim 2, wherein the second light source is configured to generate radiation having a radiation concentration of at least 12 mJ/cm$^2$.

4. The disinfection system of claim 1, wherein the at least one identification unit is a camera or a radar.

5. The disinfection system of claim 1, wherein at least one of the first light source and the second light source is comprised in a single lighting unit or is comprised in separate lighting units.

6. The disinfection system of claim 1, wherein the first time period is longer than the second time period.

7. A vehicle, comprising:
an interior; and
a disinfection system comprising
a first light source configured to generate radiation in a range of 100-300 nm;
a second light source configured to generate radiation in a range of 210-230 nm;
at least one identification unit configured to identify whether there are passengers in the vehicle; and a controller configured to control the first and second light sources based on whether there are passengers in the vehicle so that when there are no passengers in the vehicle the controller activates the first light source for a first period of time and when there are passengers in the vehicle the controller activates the second light source for a second period of time,
wherein the first and second light sources are fixed on a roof in the interior of the vehicle, on a bearing pillar of the vehicle, or on a console of the vehicle.

8. The vehicle of claim 7, wherein the first and second light sources are arranged next to each other such that a radiation propagation of the first light source and a radiation propagation of the second light source are identical within the interior of the vehicle.

9. The vehicle of claim 7, wherein the first time period is longer than the second time period.

10. A method for controlling a disinfection system of a vehicle, the method comprising:
determining, by a controller of the disinfection system, whether there are passengers in the vehicle based on information provided by at least one identification unit; and
switching on one of a first and second light source depending on whether or not there are passengers in the vehicle,
wherein the first and second light sources are arranged in an interior of the vehicle, wherein the first light source is configured to generate radiation in a range of 100-300 nm, and wherein the second light source is configured to generate radiation in a range of 210-230 nm, and
wherein the first light source is switched on for a first period of time when there are no passengers in the vehicle and the second light source is switched on for a second period of time when there are passengers in the vehicle.

11. The method of claim 10, wherein the at least one identification unit is a camera or a radar.

12. The method of claim 10, wherein the first period of time is at least 6 seconds and the second period of time is at least 2.5 seconds.

13. The method of claim 10, wherein the first period of time is longer than the second period of time.

* * * * *